US008795640B2

(12) United States Patent
Mendoza

(10) Patent No.: US 8,795,640 B2
(45) Date of Patent: Aug. 5, 2014

(54) LIP FORMULATION

(71) Applicant: Mary Kay Inc., Dallas, TX (US)

(72) Inventor: Ricky Mendoza, Fort Worth, TX (US)

(73) Assignee: Mary Kay Inc., Dallas, TX (US)

( * ) Notice: Subject to any disclaimer, the term of this patent is extended or adjusted under 35 U.S.C. 154(b) by 24 days.

(21) Appl. No.: 13/724,086

(22) Filed: Dec. 21, 2012

(65) Prior Publication Data
US 2013/0164229 A1 Jun. 27, 2013

Related U.S. Application Data

(60) Provisional application No. 61/579,509, filed on Dec. 22, 2011.

(51) Int. Cl.
A61K 8/97 (2006.01)

(52) U.S. Cl.
USPC .......................................................... 424/59

(58) Field of Classification Search
None
See application file for complete search history.

(56) References Cited

U.S. PATENT DOCUMENTS

| 2,798,053 | A | | 7/1957 | Brown ............................. 521/38 |
|---|---|---|---|---|
| 4,509,949 | A | | 4/1985 | Huang et al. ...................... 8/558 |
| 4,599,379 | A | | 7/1986 | Flesher et al. ................. 524/801 |
| 4,628,078 | A | | 12/1986 | Glover et al. .............. 526/303.1 |
| 4,835,206 | A | | 5/1989 | Farrar et al. .................... 524/457 |
| 4,849,484 | A | | 7/1989 | Heard ............................ 525/221 |
| 5,087,445 | A | | 2/1992 | Haffey et al. ...................... 424/59 |
| 5,100,660 | A | | 3/1992 | Hawe et al. ................. 424/78.35 |
| 5,215,749 | A | | 6/1993 | Nicoll et al. .................... 424/401 |
| 5,667,765 | A | | 9/1997 | Hansenne et al. ............... 424/59 |
| 5,753,266 | A | | 5/1998 | Youssefyeh et al. .......... 424/484 |
| 5,804,168 | A | | 9/1998 | Murad .............................. 424/59 |
| 5,843,407 | A | * | 12/1998 | El-Nokaly et al. .............. 424/64 |
| 5,961,961 | A | | 10/1999 | Dobkowski et al. ............. 424/59 |
| 5,968,519 | A | | 10/1999 | Youssefyeh et al. .......... 424/755 |
| 6,197,281 | B1 | | 3/2001 | Stewart et al. ................... 424/59 |
| 6,383,505 | B1 | * | 5/2002 | Kaiser et al. ................... 424/407 |
| 6,419,908 | B1 | | 7/2002 | Candau et al. ................... 424/59 |
| 6,485,713 | B1 | | 11/2002 | Bonda et al. ..................... 424/59 |
| 6,555,097 | B1 | | 4/2003 | Rabe et al. ....................... 424/64 |
| 6,582,748 | B1 | | 6/2003 | Loh et al. ....................... 426/601 |
| 6,599,513 | B2 | | 7/2003 | Deckers et al. ................ 424/401 |
| 6,911,211 | B2 | | 6/2005 | Eini et al. ....................... 424/401 |
| 7,014,842 | B2 | | 3/2006 | Dueva-Koganov et al. .... 424/59 |
| 7,264,795 | B2 | | 9/2007 | Pflucker et al. ................. 424/59 |
| 7,320,797 | B2 | | 1/2008 | Gupta ............................ 424/401 |
| 7,695,727 | B2 | | 4/2010 | Magee et al. .................. 424/401 |
| 7,892,524 | B2 | | 2/2011 | Polonka et al. .................. 424/59 |
| 7,902,134 | B1 | | 3/2011 | Lutrario et al. ................ 510/130 |
| 7,910,090 | B2 | | 3/2011 | Dueva-Koganov et al. .... 424/59 |
| 7,959,834 | B2 | | 6/2011 | Bonda et al. ................... 252/589 |
| 7,960,437 | B2 | | 6/2011 | Anderson et al. ............. 514/739 |
| 8,034,755 | B2 | | 10/2011 | Kawano et al. ............... 510/130 |
| 2004/0253275 | A1 | | 12/2004 | Eini et al. ....................... 424/400 |
| 2005/0004274 | A1 | * | 1/2005 | Healy et al. ...................... 524/80 |
| 2006/0057080 | A1 | | 3/2006 | Rivero et al. .................... 424/59 |
| 2006/0159716 | A1 | | 7/2006 | Themens et al. .............. 424/401 |
| 2007/0160549 | A1 | | 7/2007 | Hunt et al. ....................... 424/59 |
| 2007/0190186 | A1 | | 8/2007 | Loh et al. ....................... 424/725 |
| 2008/0085961 | A1 | | 4/2008 | Lin ................................. 524/313 |
| 2008/0145323 | A1 | | 6/2008 | Dann et al. ...................... 424/59 |
| 2008/0219938 | A1 | | 9/2008 | Grune ............................. 424/59 |
| 2008/0247977 | A1 | | 10/2008 | Le Gendre et al. ............. 424/64 |
| 2008/0292668 | A1 | | 11/2008 | Baars et al. ................... 424/401 |
| 2009/0098070 | A1 | | 4/2009 | Karpov et al. ................... 424/59 |
| 2009/0202459 | A1 | | 8/2009 | Spaulding ....................... 424/60 |
| 2009/0317344 | A1 | | 12/2009 | Zhang et al. .................... 424/64 |
| 2010/0015073 | A1 | | 1/2010 | Clavel et al. .................... 424/63 |
| 2010/0028276 | A1 | | 2/2010 | Grune ............................. 424/59 |
| 2010/0041754 | A1 | | 2/2010 | Lin ................................. 514/558 |
| 2010/0076090 | A1 | | 3/2010 | Holyfield ....................... 514/690 |
| 2010/0119463 | A1 | | 5/2010 | Jacobs ............................. 424/59 |
| 2010/0226867 | A1 | | 9/2010 | Dueva-Koganov et al. .... 424/60 |
| 2010/0316664 | A1 | | 12/2010 | Iino et al. ................... 424/195.16 |
| 2011/0110988 | A1 | | 5/2011 | Susak et al. ................... 424/401 |
| 2011/0212040 | A1 | | 9/2011 | Von Oppen Bezalel et al. ................................ 424/60 |
| 2011/0244030 | A1 | | 10/2011 | Lebel ............................. 424/450 |
| 2011/0250250 | A1 | * | 10/2011 | Kishida et al. ................ 424/401 |
| 2012/0034320 | A1 | | 2/2012 | Murray et al. ................. 424/678 |

FOREIGN PATENT DOCUMENTS

| EP | 0456458 | 11/1991 |
|---|---|---|
| EP | 0512040 | 11/1992 |
| EP | 1011623 | 6/2000 |
| EP | 1083871 | 3/2001 |
| EP | 1093797 | 4/2001 |
| EP | 1411888 | 4/2004 |

(Continued)

OTHER PUBLICATIONS

Lubrizol Schercemol Esters [online], archived Aug. 11, 2009 and retrieved on Sep. 20, 2013 from URL<http://web.archive.org/web/20090811003439/http://www.lubrizol.com/PersonalCare/Products/EssentialEsters/SchercemolEsters/>.*

(Continued)

Primary Examiner — Abigail Fisher
Assistant Examiner — Daniel L Branson
(74) Attorney, Agent, or Firm — Fulbright & Jaworski LLP

(57) ABSTRACT

Disclosed is an anhydrous lip product and methods of its use that include a gellant comprising *Helianthus annuus* oil, *Carthamus tinctorius* oil, and styrene/butadiene copolymer, a combination of UV sunscreen agents comprising octocrylene, avobenzone, and octinoxate, a combination of moisturizers comprising pentaerythrityl tetra-isostearate, cetyl ethylhexanoate, and C12-15 alkyl benzoate, and a combination of antioxidants comprising tocopheryl acetate and tocopherol, wherein the lip product has a sun protection factor of around 15 to 20.

12 Claims, No Drawings

(56) References Cited

FOREIGN PATENT DOCUMENTS

| | | |
|---|---|---|
| EP | 1722858 | 11/2006 |
| EP | 1799184 | 6/2007 |
| WO | WO 98/52525 | 11/1998 |
| WO | WO 98/55086 | 12/1998 |
| WO | WO 99/62476 | 12/1999 |
| WO | WO 03/011239 | 2/2003 |
| WO | WO 2004/110366 | 12/2004 |
| WO | WO 2005/074867 | 8/2005 |
| WO | WO 2006/031833 | 3/2006 |
| WO | WO 2007/006536 | 1/2007 |
| WO | WO 2007/075747 | 7/2007 |
| WO | WO 2008/031065 | 3/2008 |
| WO | WO 2008/108756 | 9/2008 |
| WO | WO 2009/032146 | 3/2009 |
| WO | WO 2009/038710 | 3/2009 |
| WO | WO 2009/077356 | 6/2009 |
| WO | WO 2009/111169 | 9/2009 |
| WO | WO 2011/008526 | 1/2011 |

OTHER PUBLICATIONS

Bonda, C., "Research Pathways to Photostable Sunscreens", Cosmetics & Toiletries, (2008), vol. 123, No. 22, p. 1, 49-60.*

International Ingredient Dictionary Handbook, $12^{th}$ Edition, vol. 1, pp. 1136-1139, 2008.

International Ingredient Dictionary Handbook, $12^{th}$ Edition, vol. 1, pp. 440-444, 2008.

* cited by examiner

LIP FORMULATION

CROSS REFERENCE TO RELATED APPLICATIONS

This application claims the benefit of U.S. Provisional Application No. 61/579,509, filed Dec. 22, 2011. The contents of the referenced application are incorporated into the present application by reference.

BACKGROUND OF THE INVENTION

A. Field of the Invention

The present invention relates generally to lip-based compositions such as lipsticks, lip balms, and lip glosses. A lip-based composition of the present invention has the ability to protect the lips from ultraviolet A and B (UVA and UVB) radiation while also moisturizing the lips to prevent cracked, dried, or chapped lips.

B. Description of Related Art

Previous attempts at lip-based products such as lip sticks have either lacked substantivity, tended to dry-out and clump or crack on the lip, or lacked the ability to effectively treat or prevent lip-related conditions (e.g., dried, cracked, chapped lips, etc.). Attempts to solve these problems have lead to formulations that were difficult to spread on the lips, had unpleasant tactile properties (e.g., heavy, oily, tacky, etc.), and had limited beneficial effects for lip-related conditions.

SUMMARY OF THE INVENTION

The inventor found a solution to the aforementioned problems. This solution results in a lip-based product such as lipstick that is substantive, does not pool on the lips, is easy to spread, and has effective amounts of actives to moisturize the lips and treat dry, chapped, or cracked lips, while also protecting the lips from the deleterious effects of the sun's UV radiation. These effects are achieved by a unique combination of: (1) an aesthetically pleasing gellant; (2) UV sunscreen agents; (3) lip moisturizers; and (4) antioxidants. The formulation can be transparent, translucent, clear, opaque, water-resistant, and can be used as a base or primer in which additional products (e.g., colored lipsticks or colored lip glosses) are applied on top of the lip formulation of the present invention.

In one aspect there is disclosed an anhydrous lip product comprising a gellant comprising *Helianthus annuus* oil, *Carthamus tinctorius* oil, and styrene/butadiene copolymer, a combination of UV sunscreen agents comprising octocrylene, avobenzone, and octinoxate, a combination of moisturizers comprising pentaerythrityl tetra-isostearate, cetyl ethylhexanoate, and C12-15 alkyl benzoate, and a combination of antioxidants comprising tocopheryl acetate and tocopherol, wherein the lip product has a sun protection factor of 15 to 30 or within 15 to 20 or within 15 to 17, or within about 15. The anhydrous lip product can include 5 to 8% by weight of the gellant, 7 to 12% by weight of the combination of UV sunscreen agents, 25 to 35% by weight of the combination of moisturizers, and 0.1 to 1% by weight of the combination of antioxidants. In certain aspects, the lip product includes 5 to 8% by weight of the gellant, 4 to 6% by weight of octocrylene, 2 to 3% by weight of avobenzone, 1 to 3% by weight of octinoxate, 15 to 20% by weight of pentaerythrityl, 7 to 12% by weight of cetyl ethylhexanoate, 3 to 5% by weight of C12-15 alkyl benzoate, 0.1 to 0.5% by weight of tocopheryl acetate, and 0.1 to 0.5% by weight of tocopherol. The anhydrous lip product can also include a combination of structuring agents comprising ozokerite, ceresine, and cetyl alcohol. In certain embodiments, the lip product includes 7 to 12% by weight of ozokerite, 3 to 7% by weight of ceresine, and 2 to 5% by weight of cetyl alcohol. The combination of structuring agents further comprises a vegetable oil (e.g., sunflower seed oil), which can be present within the composition in an amount of 30 to 35% by weight of the composition. The lip product can also include ethyhexyl methoxycrylene, which can be present in an amount ranging between 0.5 to 2% by weight of the composition. The lip product can be a gel. The lip product can have a semi-solid or solid form. The lip product can be transparent, translucent, opaque, clear, or colorless. In certain aspects, it appears "invisible" when applied to lips, which indicates a transparent, clear, and colorless product. In certain aspects, the gellant consists of *Helianthus annuus* oil, *Carthamus tinctorius* oil, and styrene/butadiene copolymer. In certain aspects, the combination of UV sunscreen agents consist of octocrylene, avobenzone, and octinoxate, and ethyhexyl methoxycrylene can be used in sufficient amounts to stabilize avobenzone or octinoxate or both. In certain aspects, the combination of moisturizers consist of pentaerythrityl tetra-isostearate, cetyl ethylhexanoate, and C12-15 alkyl benzoate. In certain aspects, the combination of antioxidants consist of tocopheryl acetate and tocopherol. In one embodiment, the anhydrous lip product is formed into an elongated lipstick stick and comprised in a lipstick container having a base and cap and capable of pushing the lipstick in a vertical direction with respect to the base. In some instances, the lip product is contained within an elongated lipstick container or an elongated container having a rounded applicator tip (e.g., concave surface, which allows for easier application to lips).

The viscosity of the lip product can be of a nature that the lip product is in a semi-solid form and can be molded into a desired shape (e.g., placement into a lipstick container and having and maintaining an elongated shape).

It is also contemplated that the viscosity of the lip-based compositions can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, cps, etc., as measured on a Brookfield Viscometer using a TC spindle at 2.5 rpm at 25° C.)). The compositions in non-limiting aspects can have a pH of about 6 to about 9. In other aspects, the pH can be 1, 2, 3, 4, 5, 6, 7, 8, 9, 10, 11, 12, 13, or 14.

The lip-based products can have a cosmetically or pharmaceutically elegant feel such a non-oily, non-greasy, non-sticky, non-tacky, and/or silky feel after being applied to skin such as hand skin.

Also disclosed is a method for treating dried, cracked, or chapped lips or skin in the vermillion border or preventing or reducing the appearance of lip wrinkles or wrinkles in the vermillion border, or erythemic (i.e., red or inflamed skin) in the vermillion border, comprising topically applying any one of the lip-based compositions disclosed in this application or any one of the mixtures disclosed in this application to dried, cracked, or chapped lips or to skin in need of prevention or reduction of lip wrinkles, wherein topical application of the compositions or mixtures treats dried, cracked, or chapped lips or prevents or reduces the appearance of lip wrinkles The composition can be applied directly onto the lips or can be used as a base for which another lip product can be applied on top of the composition. The lip-based compositions can also be used to increase the production of collagen and hyaluronic acid in the lips via topical application of the composition to lips in need of increased collagen production and hyaluronic acid production.

"Vermillion border" means the normally sharp demarcation between the lip (red colored) and the adjacent normal skin. It represents the change in the epidermis from highly keratinized external skin to less keratinized internal skin. It typically has no sebaceous glands, sweat glands, or hair.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

One of the unique aspects of the present invention is a lip-based formulation such as an anhydrous lipstick that has a pleasant tactile property along with effective moisturizing and SPF capabilities. The effectiveness of the composition resides in the synergistic combination of a gellant, a combination of UV sunscreen agents, a combination of moisturizing agents, and a combination of antioxidants.

These and other aspects of the present invention are described in further detail below.

A. Gellant

A wide variety of gellants, which are used to produce gelling in compositions, are available. The inventor discovered that a commercially available gellant in combination with the additional ingredients discussed throughout this specification produces a unique lip product. This commercial gellant includes a combination of *Helianthus annuus* oil, *Carthamus tinctorius* oil, and a styrene/butadiene copolymer. It is sold under the trade name NatureVgel™ EG 100 by Applechem, Inc. (Newark, N.J., USA). The gellant can be used in amounts ranging from 5 to 8% by weight of the composition.

B. UV Sunscreen Agents

UV absorbing agents are capable of protecting skin from UV radiation (e.g., UVA, UVB, and/or UVC radiation). Non-limiting examples of UV Absorbing Agents that can be used in the context of the present invention include those listed in the International Cosmetic Ingredient Dictionary Handbook, 12$^{th}$ Edition (2008), Vol. 3, pages 3236-3239, which is incorporated by reference. Such examples include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (and octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, dibenzoylmethane derivatives (e.g., avobenzone), styrene/acrylates copolymer (e.g., SUNSPHERES™ sold by Rohm and Haas), octocrylene, etc. Non-limiting examples of physical sunblocks include, kaolin, talc, petrolatum and metal oxides (e.g., titanium dioxide and zinc oxide).

The inventor discovered that a particular combination of UV absorbing ingredients work best in the context of the present invention. This combination includes octocrylene, avobenzone, and octinoxate. The amount of the total combination of UV ingredients can range between 7 to 12% by weight of the composition. In particular aspects, the amount of each ingredient can be 4 to 6% by weight of octocrylene, 2 to 3% by weight of avobenzone, and 1 to 3% by weight of octinoxate. To ensure sufficient stability of the avobenzone and/or octinoxate within the composition, an amount of 0.5 to 2% by weight of ethylhexyl methoxycrylene (sold by Hallstar (USA) under the trade name SolaStay® S1) can be used.

C. Moisturizers

A wide range of moisturizers can be used. However, the inventor discovered that a particular combination of moisturizes works well in the context of the present invention. This combination includes pentaerythrityl tetraisostearate, cetyl ethylhexanoate, and C12-15 alkyl benzoate, each of which are described in the International Cosmetic Ingredient Dictionary Handbook, 12$^{th}$ Edition (2008), which is incorporated by reference. In particular aspects, the total amount of moisturizers within the composition is 25 to 35% by weight of the composition. In even more particular aspects, the following individual ranges can be used: 15 to 20% by weight of pentaerythrityl tetraisostearate; 7 to 12% by weight of cetyl ethylhexanoate; and 3 to 5% by weight of C12-15 alkyl benzoate.

D. Antioxidants

A wide range of antioxidants can be used. However, the inventor discovered that a particular combination of antioxidants works well in the context of the present invention. This combination includes tocopherol and tocopheryl acetate, both of which are described in the International Cosmetic Ingredient Dictionary Handbook, 12$^{th}$ Edition (2008), which is incorporated by reference. In particular aspects, the total amount of antioxidants within the composition can range from 0.1 to 1% by weight of the composition. In certain aspects, the amount of each antioxidant can be 0.1 to 0.5% by weight of the composition of tocopheryl acetate and 0.1 to 0.5% by weight of the composition of tocopherol.

E. Structuring Agents

Structuring agents can be used to provide the appropriate viscosity of the composition and to ensure stability of the composition. The inventor discovered that a particular combination of structuring agents works well in the context of the present invention. This combination includes ozokerite, ceresine, and cetyl alcohol. In particular aspects, a vegetable oil (e.g., sunflower seed oil) can also be used. The total amount of structuring agents can range from 12 to 50% of the total weight of the composition. In particular aspects, 7 to 12% by weight of ozokerite, 3 to 7% by weight of ceresine, and 2 to 5% by weight of cetyl alcohol can be used. In further embodiments, 30 to 35% by weight of the vegetable oil can be used.

F. Amounts of Combinations

The amounts of the gellants, UV sunscreen agents, moisturizers, antioxidants, structuring agents, and additional ingredients can vary. For instance, these ingredients can each individually be included in the composition in amounts w/w ranging from 0.0001, 0.001, 0.01, 0.1, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90% or more. However, in certain aspects, the inventor found that the following works best in the context of the present invention: 5 to 8% by weight of the gellant; 4 to 6% by weight of octocrylene; 2 to 3% by weight of avobenzone; 1 to 3% by weight of octinoxate; 15 to 20% by weight of pentaerythrityl; 7 to 12% by weight of cetyl ethylhexanoate; 3 to 5% by weight of C12-15 alkyl benzoate; 0.1 to 0.5% by weight of tocopheryl acetate; and 0.1 to 0.5% by weight of tocopherol. In further aspects, 30 to 35% by weight of the vegetable oil along with 0.5 to 2% by weight of ethyhexyl methoxycrylene, 7 to 12% by weight of ozokerite, 3 to 7% by weight of ceresine, and 2 to 5% by weight of cetyl alcohol can be used.

Further additional ingredients such as cosmetic or pharmaceutical ingredients can be added into the lip formulations of the present invention. Such additional ingredients can be added in amounts ranging from 0.0001, 0.001, 0.01, 0.1, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90% or more or any range derivable therein. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

G. Additional Ingredients

In addition to the above-mentioned ingredients, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. Additional Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *althea officinalis* extract, apricot (*prunus armeniaca*) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota* sativa) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (citrus medica limonum) oil, linoleic acid, linolenic acid, macadamia ternifolia nut oil, maltitol, matricaria (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (citrus aurantium dulcis) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus* dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

b. Additional Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

c. Additional Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof d. Silicone Containing Compounds In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

e. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

f. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof g. Preservatives Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof 2. Pharmaceutical Ingredients Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

H. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Lip Balm Formulation

The Table 1 composition is a non-limiting guideline of a lip balm of the present invention.

TABLE 1*

| Phase** | Ingredient | Amount (% w/w) |
|---|---|---|
| A | Gellant** | 5 to 8 |
| | Vegetable Oil*** | 30 to 35 |
| | Pentaerythrityl Tetraisostearate | 15-20 |
| | Cetyl Ethylhexanoate | 7 to 12 |
| | C12-15 Alkyl Benzoate | 3 to 5 |
| B | Ozokerite | 7 to 12 |
| | Ceresine | 3 to 7 |
| | Cetyl Alcohol | 2 to 5 |
| C | Octocrylene | 4 to 6 |
| | Ethylhexyl Methoxycrylene | 0.5 to 2 |
| | Avobenzone | 2 to 3 |
| | Octinoxate | 1 to 3 |
| D | Tocopheryl Acetate | 0.1 to 0.5 |
| | Tocopherol | 0.1 to 0.5 |
| | TOTAL | 100 |

*As indicated in the amount % column of Table 1, the amount of the ingredients can vary. Composition can be prepared by mixing the phase A ingredients under heat (80-85° C.) for 10 -15 minutes until uniform. Add phase B ingredients and continue mixing under heat until mixture is homogenous. Add phase C ingredients and continue mixing under heat until mixture is homogenous. Add phase D ingredients and continue mixing under heat until homogenous. Cool mixture to 70-75° C. and pour into lipstick tube or lip gloss or lip balm container and cool to room temperature (20-25° C.). Formulation should be in semi-solid form.
**Gellant used was NatureVgel ™ EG 100 from Applechem, Inc. (Newark, NJ, USA).
***Vegetable Oil used was sunflower seed oil.

A formulation having about 7.5% w/w of gellant, 33% w/w of vegetable oil, 16% w/w of pentaerythrityl tetraisostearate, 10% w/w cetyl ethylhexanoate, 3.7% w/w of C12-15 alkyl benzoate, 11% w/w ozokerite, 5.5% w/w of ceresin, 1% w/w cetyl alcohol, 6% w/w octocrylene, 1%w/w ethylhexyl methoxycrylene, 2.5% w/w avobenzone, 2% w/w octinoxate, 0.5% w/w tocopheryl acetate and tocopherol resulted in a formulation having an SPF of about 15 that was also capable of being used alone or under lipstick or lip gloss (e.g., such as a primer).

Example 2

Prophetic Examples

Additional efficacy data points of compositions of the present inventions can be determined by methods known to those of ordinary skill in the art. The following are non-limiting procedures that can be used in the context of the present invention. It should be recognized that other testing procedures can be used, including, for example, objective and subjective procedures.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control. This test can also be used to confirm the skin exfoliation abilities of the composition (e.g., stain skin and then treat stained skin with composition to determine amount of stain removed over a targeted time period).

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether the product is inducing irritation. The measurements were made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. Skin clarity is defined as L/C where C is chroma and is defined as $(a^2+b^2)^{1/2}$.

* * *

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An anhydrous lip product comprising:
 (a) 5 to 8% by weight of a gellant comprising *Helianthus annuus* oil, *Carthamus tinctorius* oil, and styrene/butadiene copolymer;
 (b) a combination of UV sunscreen agents comprising 4 to 6% by weight of octocrylene, 2 to 3% by weight of avobenzone, and 1 to 3% by weight of octinoxate;
 (c) a combination of moisturizers comprising 15 to 20% by weight of pentaerythrityl tetraisostearate, 7 to 12% by weight of cetyl ethylhexanoate, and 3 to 5% by weight of C12-15 alkyl benzoate; and
 (d) a combination of antioxidants comprising 0.1 to 0.5% by weight of tocopheryl acetate and 0.1 to 0.5% by weight of tocopherol,
 wherein the lip product has a sun protection factor of around 15 to 20.

2. The anhydrous lip product of claim 1, further comprising a combination of structuring agents comprising ozokerite, ceresine, and cetyl alcohol.

3. The anhydrous lip product of claim 2, comprising:
 7 to 12% by weight of ozokerite;
 3 to 7% by weight of ceresine; and
 2 to 5% by weight of cetyl alcohol.

4. The anhydrous lip product of claim 3, wherein the combination of structuring agents further comprises a vegetable oil.

5. The anhydrous lip product of claim 4, wherein the vegetable oil is sunflower seed oil.

6. The anhydrous lip product of claim 5, comprising 30 to 35% by weight of the vegetable oil.

7. The anhydrous lip product of claim 6, further comprising 0.5 to 2% by weight of ethyhexyl methoxycrylene.

8. The anhydrous lip product of claim 1, wherein the gellant consists of *Helianthus annuus* oil, *Carthamus tinctorius* oil, and styrene/butadiene copolymer.

9. The anhydrous lip product of claim 8, wherein the combination of UV sunscreen agents consist of octocrylene, avobenzone, and octinoxate.

10. The anhydrous lip product of claim 1, comprising ethyhexyl methoxycrylene in sufficient amounts to stabilize avobenzone or octinoxate or both.

11. The anhydrous lip product of claim 10, wherein the combination of moisturizers consist of pentaerythrityl tetraisostearate, cetyl ethylhexanoate, and C12-15 alkyl benzoate.

12. The anhydrous lip product of claim 11, wherein the combination of antioxidants consist of tocopheryl acetate and tocopherol.

* * * * *